US00PP33269P2

(12) United States Plant Patent
Koning

(10) Patent No.: US PP33,269 P2
(45) Date of Patent: Jul. 13, 2021

(54) ***LAVANDULA* PLANT NAMED 'ANOUK DELUXE 1225'**

(50) Latin Name: *Lavandula stoechas*
Varietal Denomination: Anouk Deluxe 1225

(71) Applicant: Lammert Koning, Nuis (NL)

(72) Inventor: Lammert Koning, Nuis (NL)

(73) Assignee: L. KONING BEHEER B.V., Nuis (NL)

( * ) Notice: Subject to any disclaimer, the term of this patent is extended or adjusted under 35 U.S.C. 154(b) by 0 days.

(21) Appl. No.: 16/873,599

(22) Filed: May 14, 2020

(51) Int. Cl.
*A01H 5/02* (2018.01)
*A01H 6/50* (2018.01)

(52) U.S. Cl.
USPC ..... Plt./445
CPC ..... *A01H 6/502* (2018.05)

(58) Field of Classification Search
USPC ..... Plt./445
CPC ..... A01H 5/02
See application file for complete search history.

(56) References Cited

U.S. PATENT DOCUMENTS

PP18,046 P2 * 9/2007 Koning ..... A01H 5/02 Plt./445
PP20,068 P2 * 6/2009 Koning ..... A01H 5/02 Plt./445

OTHER PUBLICATIONS https://www.floraldaily.com/article/9171098/leading-the-lavender-revolution/; Dec. 19, 2019; 2 pages.*
https://www.darwinperennials.com/Products/Plantinfo/?phid=037301435019542; Sep. 29, 2020; 2 pages.*

* cited by examiner

*Primary Examiner* — Kent L Bell
(74) *Attorney, Agent, or Firm* — C. Anne Whealy

(57) ABSTRACT

A new and distinct cultivar of *Lavandula* plant named 'Anouk Deluxe 1225', characterized by its upright and broadly spreading plant habit; freely branching growth habit; freely flowering habit; no requirement for a vernalization period for flowering; dark purple-colored flowers and purple-colored terminal flower bracts positioned on strong and erect peduncles; long flowering period; and good post-production and garden performance.

1 Drawing Sheet

Botanical designation: *Lavandula stoechas.*
Cultivar denomination: 'ANOUK DELUXE 1225'.

BACKGROUND OF THE INVENTION

The present invention relates to a new and distinct *Lavandula* plant, botanically known as *Lavandula stoechas*, commonly referred to as Lavender and hereinafter referred to by the name 'Anouk Deluxe 1225'.

The new *Lavandula* plant is a product of a planned breeding program conducted by the Inventor in Nuis, The Netherlands and Boskoop, The Netherlands. The objective of the breeding program was to develop new unique *Lavandula* plants with good performance and attractive plant form and flower coloration.

The new *Lavandula* plant originated from an open-pollination in May, 2015 of *Lavandula stoechas* 'Anouk', disclosed in U.S. Plant Pat. No. 16,685, as the female, or seed, parent with an unknown proprietary selection of *Lavandula stoechas* as the male, or pollen, parent. The new *Lavandula* plant was discovered and selected by the Inventor as a single flowering plant within the progeny of the stated open-pollination in a controlled environment in Nuis, The Netherlands in May, 2016.

Asexual reproduction of the new *Lavandula* plant by terminal cuttings in a controlled greenhouse environment in Boskoop, The Netherlands since August, 2016 has shown that the unique features of this new *Lavandula* plant are stable and reproduced true to type in successive generations.

SUMMARY OF THE INVENTION

Plants of the new *Lavandula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Lavandula* plant. These characteristics in combination distinguish 'Anouk Deluxe 1225' as a new and distinct *Lavandula* plant:

1. Upright and broadly spreading plant habit.
2. Freely branching growth habit.
3. Freely flowering habit; plants do not require a vernalization period for flowering.
4. Dark purple-colored flowers and purple-colored terminal flower bracts positioned on strong and erect peduncles.
5. Long flowering period.
6. Good postproduction and garden performance.

Plants of the new *Lavandula* differ primarily from plants of the female parent, 'Anouk', in the following characteristics:

1. Plants of the new *Lavandula* are larger and bushier than plants of 'Anouk'.
2. Plants of the new *Lavandula* do not require a vernalization period for flowering whereas plants of 'Anouk' require a vernalization period for flowering.
3. Plants of the new *Lavandula* have dark purple-colored flowers and purple-colored terminal flower bracts whereas plants of 'Anouk' have purple violet-colored flowers and violet-colored terminal flower bracts.

Plants of the new *Lavandula* can be compared to plants of the *Lavandula stoechas* 'Silver Anouk', disclosed in U.S. Plant Pat. No. 20,068. In side-by-side comparisons, plants of the new *Lavandula* differ primarily from plants of 'Silver Anouk' in the following characteristics:

1. Plants of the new *Lavandula* are larger and bushier than plants of 'Silver Anouk'.
2. Plants of the new *Lavandula* do not require a vernalization period for flowering whereas plants of 'Silver Anouk' require a vernalization period for flowering.
3. Plants of the new *Lavandula* have dark purple-colored flowers and purple-colored terminal flower bracts whereas plants of 'Silver Anouk' have dark violet-colored flowers and purple-colored terminal flower bracts.

Plants of the new *Lavandula* can also be compared to plants of the *Lavandula stoechas* 'Toscane', disclosed in U.S. Plant Pat. No. 18,046. In side-by-side comparisons, plants of the new *Lavandula* differ primarily from plants of 'Toscane' in the following characteristics:

1. Plants of the new *Lavandula* are larger and bushier than plants of 'Toscane'.
2. Plants of the new *Lavandula* do not require a vernalization period for flowering whereas plants of 'Toscane' require a vernalization period for flowering.
3. Plants of the new *Lavandula* have dark purple-colored flowers and purple-colored terminal flower bracts whereas plants of 'Toscane' have purple-colored flowers and light violet-colored terminal flower bracts.

BRIEF DESCRIPTION OF THE PHOTOGRAPH

The accompanying photograph illustrates the overall appearance of the new *Lavandula* plant showing the colors as true as it is reasonably possible to obtain in colored reproductions of this type. Colors in the photograph may differ slightly from the color values cited in the detailed botanical description which accurately describe the colors of the new *Lavandula* plant.

The photograph (FIG. 1) is a side perspective view of a typical flowering plant of 'Anouk Deluxe 1225' grown in a container.

DETAILED BOTANICAL DESCRIPTION

Plants used in the aforementioned photograph and following detailed description were grown in 12-cm containers during the late spring in an outdoor nursery in Boskoop, The Netherlands and under cultural practices typical of commercial *Lavandula* production. Plants were pinched one time and were ten months old when the photograph and description were taken. During the production of the plants, day temperatures ranged from 10° C. to 30° C. and night temperatures ranged from 5° C. to 20° C. In the following description, color references are made to The Royal Horticultural Society Colour Chart, 2015 Edition, except where general terms of ordinary dictionary significance are used.

Botanical classification: *Lavandula stoechas* 'Anouk Deluxe 1225'.

Parentage:

*Female, or seed, parent.*—*Lavandula stoechas* 'Anouk', disclosed in U.S. Plant Pat. No. 16,685.

*Male, or pollen, parent.*—Unknown proprietary selection of *Lavandula stoechas*, not patented.

Propagation:

*Type.*—Terminal vegetative cuttings.

*Time to initiate roots, summer and winter.*—About ten days at temperatures about 18° C.

*Time to produce a rooted young plant, summer.*—About 60 days at temperatures about 20° C.

*Time to produce a rooted young plant, winter.*—About 70 days at temperatures about 20° C.

*Root description.*—Fine, fibrous; initially white in color and becoming more brown with development; actual color of the roots is dependent on substrate composition, water quality, fertilizer type and formulation.

*Rooting habit.*—Freely branching; dense.

Plant description:

*Plant and growth habit.*—Herbaceous perennial; upright and broadly spreading plant habit; flattened globular plant shape; freely branching habit; moderately vigorous growth habit; moderate growth rate; flowers arranged in verticillasters on crowded spikes with showy terminal flower bracts.

*Plant height, soil level to top of foliar plane.*—About 15.5 cm.

*Plant height, soil level to top of floral plane.*—About 23.5 cm.

*Plant width.*—About 27.5 cm.

*Lateral branch description.*—Quantity per plant: About 14 primary lateral branches and about 60 secondary lateral branches developing per plant. Length: About 4.8 cm. Diameter: About 1.75 mm. Internode length: About 1.7 cm. Strength: Moderately strong. Aspect: Primary lateral branches, upright to about 80° from vertical; secondary lateral branches, about 20° from primary lateral branch axis. Texture and luster: Moderately tomentose; matte. Color, when developing: Close to 144A to 144B. Color, developed: Close to 143B; with development, close to 199A and 199B.

*Leaf description.*—Arrangement: Opposite, simple; sessile. Length: About 5.2 cm. Width: About 9 mm. Shape: Narrowly oblanceolate, flat. Apex: Acute. Base: Cuneate. Margin: Entire; revolute; not lobed. Texture and luster, upper and lower surfaces: Moderately tomentose; not rugose; matte. Fragrance: Strongly aromatic, pungent. Venation pattern: Pinnate. Color: Developing leaves, upper surface: Close to 137C. Developing leaves, lower surface: Close to 138B. Fully expanded leaves, upper surface: Close to NN137C; venation, close to 144B; pubescence, close to NN155D to lighter than NN155D. Fully expanded leaves, lower surface: Close to 138A; venation, close to 143B; pubescence, close to NN155D to lighter than NN155D.

Flower description:

*Flower type, arrangement and habit.*—Small single salverform flowers arranged in compact verticillasters on crowded terminal spikes; freely flowering, about 325 flowers developing per inflorescence and more than 10,000 flowers developing per plant; flowers with two-lobed upper lip and three-lobed lower lip; flowers face mostly outwardly on the spike; inflorescences with showy terminal flower bracts.

*Natural flowering season*.—Long flowering period; continuous from late spring into the summer in The Netherlands; plants begin flowering about 13 weeks after planting; plants do not require a vernalization period for flowering.

*Flower longevity on the plant*.—Individual flowers last about four weeks on the plant; flowers not persistent.

*Fragrance*.—None detected.

*Flower buds*.—Length: About 8 mm. Diameter: About 2 mm. Shape: Elliptic. Texture and luster: Moderately tomentose; matte. Color: Close to 144B; distally, tinged with close to 177A; at the apex, close to 60C to 60D; pubescence, close to NN155D.

*Inflorescence size*.—Height: About 7 cm. Diameter, at terminal flower bracts: About 3 cm. Diameter, below flower bracts: About 1.9 cm.

*Flower size*.—Diameter: About 4.5 mm by 4.5 mm. Depth (height): About 7 mm. Throat diameter: About 1 mm. Tube length: About 6 mm. Tube diameter: About 1 mm.

*Petals*.—Quantity and arrangement: Upper lip, two-lobed and lower lip, three-lobed. Length, upper lip: About 7 mm. Length, lower lip: About 7 mm. Width, upper lip: About 1.75 mm. Width, lower lip: About 1.5 mm. Shape: Roughly spatulate; lower 72.5% fused into a tube. Apex: Obtuse, rounded. Margin: Entire; slightly undulate. Texture and luster, upper surface: Smooth, glabrous; velvety; matte. Texture and luster, lower surface: Smooth, glabrous; moderately velvety; slightly glossy. Texture, throat and tube: Moderately tomentose; matte. Color: When opening, upper and lower surfaces: Close to between N92A and 79A. Fully opened, upper and lower surfaces: Close to between N92A and 79A; venation, close to between N92A and 79A; color becoming closer to N92A with development. Throat: Close to 79B to 79C; venation, close to 78B to 79C. Tube: Close to 79C fading proximally to close to NN155C; venation, close to 79C fading proximally to close to NN155C.

*Terminal flower bracts*.—Quantity and arrangement: About seven positioned upright at inflorescence apex. Length: About 1.3 cm to 3.8 cm. Width: About 9 mm to 16 mm. Shape: Obovate to narrowly obovate. Apex: Broadly acute to obtuse. Base: Narrowly cuneate. Margin: Entire; moderately undulate. Texture and luster, upper and lower surfaces: Slightly tomentose; matte. Color, upper surface: Close to N79A, N79B, N80B and N80C; main vein, close to N77A; pubescence, close to NN155D. Color, lower surface: Close to N81B; main vein, close to 187A; pubescence, close to NN155D.

*Basal flower bracts*.—Quantity and arrangement: Each group of five flowers is subtended by a single basal flower bract. Length: About 9 mm. Width: About 9.5 mm. Shape: Broadly rhomboidal. Apex: Broadly aristate. Base: Cuneate. Margin: Entire. Texture and luster, upper and lower surfaces: Sparsely to moderately tomentose; matte. Color, upper surface: Close to 186B and 186C; venation, close to 147B; pubescence, close to NN155C. Color, lower surface: Close to 60C; venation, close to between N186C and 200A; pubescence, close to NN155C.

*Sepals*.—Quantity and arrangement: Five, fused into a campanulate tube. Calyx length: About 8 mm. Calyx diameter: About 1.75 mm. Length: About 8 mm. Width: About 0.5 mm. Shape: Lanceolate. Apex: Acute. Margin: Entire. Texture and luster, upper surface: Smooth, glabrous; matte. Texture and luster, lower surface: Densely pubescent; matte. Color: When opening and fully opened, upper surface: Close to 145A; venation, close to 146A. When opening and fully opened, lower surface: Proximally, close to 144B; distally, tinged with close to 188A; at the apex, close to 60C to 60D; pubescence, close to NN155C.

*Peduncles*.—Length: About 7.3 cm. Diameter: About 2.5 mm. Aspect: Mostly upright. Strength: Strong. Texture and luster: Moderately tomentose; matte. Color: Close to 143A and 143B; distally, tinged with close to N77A; pubescence, close to NN155D to lighter than NN155D.

*Reproductive organs*.—Stamens: Quantity per flower: Four. Filament length: About 1 mm. Filament color: Close to 77B to 77C. Anther shape: Reniform. Anther size: About 0.5 mm by 0.5 mm. Anther color: Close to 11D. Pollen amount: Scarce to moderate. Pollen color: Close to 156D. Pistils: Quantity per flower: One. Pistil length: About 5 mm. Stigma shape: Club-shaped. Stigma diameter: About 0.5 mm. Stigma color: Close to N187A. Style length: About 4 mm. Style color: Close to NN155D. Ovary color: Close to 143B to 143C.

*Seeds and fruits*.—To date, seed and fruit production has not been observed on plants of the new *Lavandula*.

Pathogen & pest resistance: To date, plants of the new *Lavandula* have not been noted to be resistant to pathogens and pests common to *Lavandula* plants.

Garden performance: Plants of the new *Lavandula* have exhibited good tolerance to rain and wind and have been observed to tolerate high temperatures about 40° C. and to be suitable for USDA Hardiness Zones 7 to 10.

It is claimed:

1. A new and distinct *Lavandula* plant named 'Anouk Deluxe 1225' as illustrated and described.

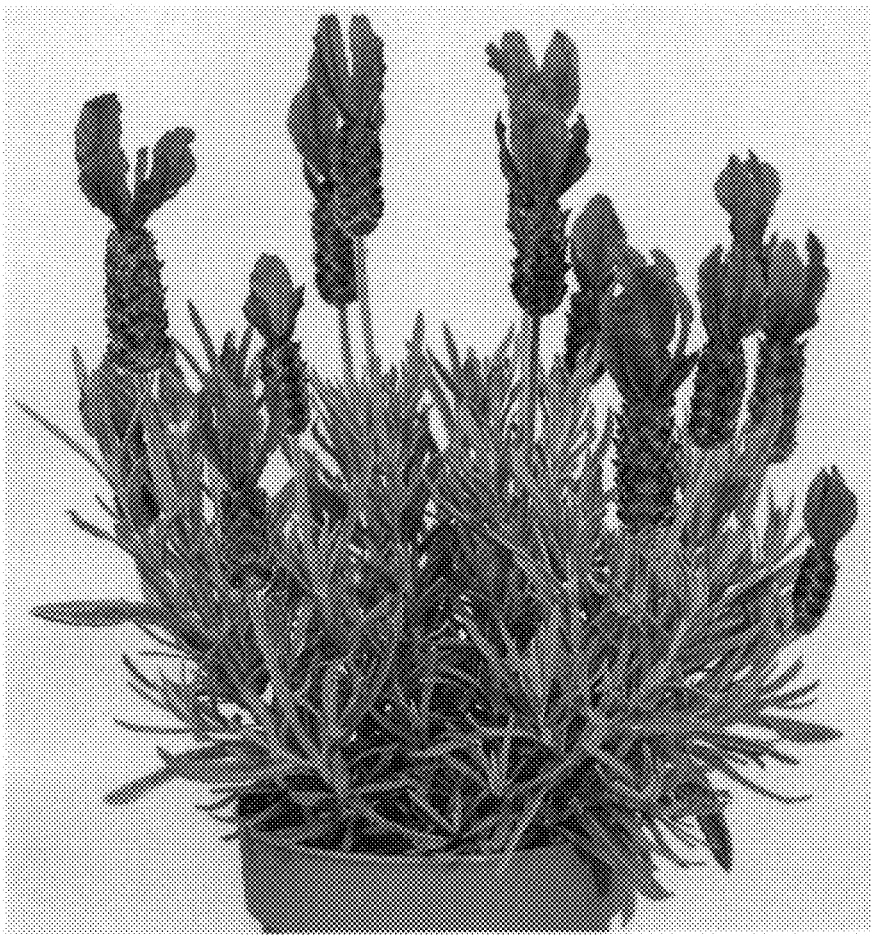

* * * * *